US011670156B2

(12) United States Patent
Weisswange et al.

(10) Patent No.: US 11,670,156 B2
(45) Date of Patent: Jun. 6, 2023

(54) INTERACTIVE REMINDER COMPANION

(71) Applicants: Honda Research Institute Europe GmbH, Offenbach/Main (DE); Sproutel Inc., Providence, RI (US)

(72) Inventors: Thomas Weisswange, Offenbach (DE); Jens Schmüdderich, Offenbach (DE); Aaron Horowitz, Providence, RI (US); Joel Schwartz, Los Angeles, CA (US)

(73) Assignees: Honda Research Institute Europe GmbH, Offenbach/Main (DE); Sproutel Inc., Providence, RI (US)

( * ) Notice: Subject to any disclaimer, the term of this patent is extended or adjusted under 35 U.S.C. 154(b) by 73 days.

(21) Appl. No.: 17/084,651

(22) Filed: Oct. 30, 2020

(65) Prior Publication Data
US 2022/0139200 A1    May 5, 2022

(51) Int. Cl.
*G08B 21/24* (2006.01)
*B25J 9/00* (2006.01)
*B25J 11/00* (2006.01)
*B25J 13/08* (2006.01)

(52) U.S. Cl.
CPC ............ *G08B 21/24* (2013.01); *B25J 9/0003* (2013.01); *B25J 11/008* (2013.01); *B25J 13/089* (2013.01)

(58) Field of Classification Search
CPC ....... G08B 21/24; B25J 9/0003; B25J 11/008; B25J 13/089; G16H 20/10; G16H 20/30; G16H 20/60; G16H 40/63
See application file for complete search history.

(56) References Cited

U.S. PATENT DOCUMENTS

| 6,337,552 B1 | 1/2002 | Inoue et al. |
| 9,390,626 B1 | 7/2016 | Horowitz et al. |
| 9,603,776 B2 | 3/2017 | Bunker et al. |

(Continued)

FOREIGN PATENT DOCUMENTS

| CN | 103217892 | 7/2013 |
| WO | 2017180066 | 10/2017 |

OTHER PUBLICATIONS

Zhi Zheng, et al., "Autonomous Robot-mediated Imitation Learning for Children with Autism," 2014 IEEE International Conference on Robotics & Automation (ICRA), vol. 68, May 2014, pp. 2707-2712.

(Continued)

*Primary Examiner* — Brian Wilson
(74) *Attorney, Agent, or Firm* — JCIPRNET (57) ABSTRACT

The present disclosure relates to a system for reminding a person to perform an activity. The system comprise a robot configured to carry out different behaviors, wherein the activity and its corresponding trigger condition are set by a user and the system selects, from the different behaviors, a first behavior assigned to the activity, senses the person, determines, based on the sensors information, whether or not the activity is performed by the person in accordance with the trigger condition. The robot carries out the selected behavior if the activity is not performed by the person in accordance with the trigger condition, wherein after or during the selected behavior is carried out, an activity of the person is determined based on the information derived from the sensors to select a second behavior from the different behaviors.

14 Claims, 4 Drawing Sheets

(56) References Cited

U.S. PATENT DOCUMENTS

| | | | |
|---|---|---|---|
| 2007/0192910 A1* | 8/2007 | Vu | B25J 19/06 |
| | | | 901/17 |
| 2009/0055019 A1 | 2/2009 | Stiehl et al. | |
| 2012/0083666 A1* | 4/2012 | Waugh | G16H 20/10 |
| | | | 600/300 |
| 2014/0125678 A1 | 5/2014 | Wang et al. | |
| 2014/0232534 A1 | 8/2014 | Birnbaum et al. | |
| 2016/0005299 A1 | 1/2016 | Zomet et al. | |
| 2016/0324726 A1 | 11/2016 | Roberts et al. | |

OTHER PUBLICATIONS

Martha E. Pollack, et al., "Autominder: An Intelligent Cognitive Orthotic System for People with Memory Impairment," Robotics and Autonomous Systems, Mar. 2003, pp. 1-10.

Matthew L. Lee, et al., "Real-time Feedback for Improving Medication Taking," CHI '14: Proceedings of the SIGCHI Conference on Human Factors in Computing Systems, Apr. 2014, pp. 1-10.

T. Shibata, et al., "Mental Commit Robot and its Application to Therapy of Children," 2001 IEEE/ASME International Conference on Advanced Intelligent Mechatronics Proceedings, Jul. 2001, pp. 1053-1058.

* cited by examiner

INTERACTIVE REMINDER COMPANION

TECHNICAL FIELD

The present disclosure relates to a system and method for reminding a person to perform certain activities.

BACKGROUND

In elderly care, systems exist that assist a person to perform a variety of tasks, such as taking medication, brushing teeth, going outside, drinking, at certain times or events. For example, a medication reminder system, which detects when a user is eating and then reminds him to take his medication, is described in US 20160005299 A1.

Further, US 20160324726 A1 discloses a pillbox, which generates an alert if the patient missed a dose or a change in the total weight of the pills after a dosing time does not match a predetermined amount.

However, reminder systems that only output an alert, spoken or displayed information and, thus require a direct response, do not easily support the user's own decisions of an exact point in time when to react. In addition, this form of reminder does not help to easily train a routine nor promote the acceptance of the task necessity.

U.S. Pat. No. 9,390,626 B1 discloses an interactive toy that shows symptoms of a chronic illness and reacts to the treatment of the symptoms using dummy medication to create empathy in a human patient and to train the treatment of the chronic illness.

However, the interactive toy merely generates symptoms corresponding to a programmed chronic illness and is not designed to remind the patient to perform certain activities at certain times.

Thus, it is an object of the present disclosure to improve the performance of a system and method for reminding a person to perform certain activities. The object is achieved by the present disclosure according to the independent claims.

SUMMARY

The present disclosure provides a system and method for reminding a person to perform certain activities.

The system according to the disclosure for reminding a person to perform at least one activity comprises a robot configured to carry out different behaviors, a setting means for setting, by a user, the at least one activity and its corresponding trigger condition for a reminder, a selecting means for selecting, from the different behaviors, a first behavior that is assigned to the at least one activity set by the user, at least one sensing means for sensing at least the person and a determining means for determining, based on information derived from the at least one sensing means, whether or not the at least one activity is performed by the person in accordance with the trigger condition.

The method according to the disclosure for reminding a person to perform at least one activity uses a robot configured to carry out different behaviors and comprises the steps of:
  setting, by a user, the at least one activity and its corresponding trigger condition for a reminder;
  selecting, from the different behaviors, a first behavior that is assigned to the at least one activity set by the user;
  sensing at least the person by at least one sensing means;
  determining, based on information derived from the at least one sensing means, whether or not the at least one activity is performed by the person in accordance with the trigger condition;
  carrying out, by the robot, the selected behavior if the at least one activity is not performed by the person in accordance with the trigger condition;
  determining, after or during the selected behavior is carried out, an activity performed by the person based on the information derived from the at least one sensing means;
  selecting, from the different behaviors, a second behavior that is assigned to the determined activity; and
  carrying out, by the robot, the second behavior.

BRIEF DESCRIPTION OF THE DRAWINGS

The disclosure will be described in the following in detail in particular with reference to the annexed drawings in which.

DETAILED DESCRIPTION

The system according to the disclosure for reminding a person to perform at least one activity comprises a robot configured to carry out different behaviors, a setting means for setting, by a user, the at least one activity and its corresponding trigger condition for a reminder, a selecting means for selecting, from the different behaviors, a first behavior that is assigned to the at least one activity set by the user, at least one sensing means for sensing at least the person and a determining means for determining, based on information derived from the at least one sensing means, whether or not the at least one activity is performed by the person in accordance with the trigger condition.

The robot is configured to carry out the selected behavior if the at least one activity is not performed by the person in accordance with the trigger condition, the determining means is configured to determine, after or during the behavior is carried out, an activity performed by the person based on the information derived from the at least one sensing means, and the selecting means is configured to select, from the different behaviors, a second behavior that is assigned to the determined activity.

With the present disclosure, the reminder is generated by the system if the person does not perform the activity in accordance with the trigger condition, wherein robot communicates the reminder to the person or their partners by carrying out the behavior assigned to the missed activity. Since the robot communicates through its behavior, the robot stimulates many senses, requires little concentration, helps to train a routine for performing the activity and prevents the feeling of loneliness and social isolation.

Activities that the person could be reminded could be: taking medication, sleeping, eating, eating specific food, drinking, leaving for an appointment, calling a certain person, washing hands, showering, brushing teeth, going for a walk, doing physical or mental exercises, getting dressed, cleaning, feeding the real pets, watering plants, cooking and/or awaiting guests.

The behavior can symbolize the activity to be performed by the person or indicates a need or symptoms of the robot, wherein an activity of the person (e.g. a certain interaction with the robot) necessary to fulfill the need or to alleviate the symptoms is related to the activity. In this way, the robot encourages the person to perform the activity for herself.

Examples for the robot needs and the corresponding behaviors could be:
Need for medication→whimpering;
Need for going for a walk→moving to entrance door/scratching on door;
Need for drinking→panting, moving to/around bottle;
Need for getting dressed→shivering, pulling current closing of human;
Need for watering the plants→sitting in front of plants with sad face; and/or
Need for keeping a regular drinking schedule→generally move slower.

Examples for need fulfillment person-robot interactions could be:
Need for medication→show medication QR code to the robot
Need for eating→charge robot through plug in its mouth
Need for sleeping→put robot in its sleeping box
Need for exercises→throw a ball for the robot to be retrieved
Need for drinking→fill a bottle-like object with water that the robot can interact with (might in parallel act as humidifier) OR→drink a glass of water in front of the robot OR→perform a certain action related to drinking, e.g. open the tab; take a glass from the shelf or open the fridge.

All or a part of activities/reminders selectable by the user (consumer), the robot needs, the corresponding behaviors and/or the corresponding person-robot interactions for need fulfillment can be determined/stored by the manufacturer and/or can be manually set/adapted by the user (consumer). Alternatively or in addition, the corresponding behaviors and/or the corresponding person-robot interactions can be determined by a machine learning method trained with person-robot interactions and/or the success rate of the reminder (amount of time the activity is performed in accordance with the reminder condition when the activity is stimulated by the respective robot behavior and/or the respective person-robot interaction).

The process of selecting, from the different behaviors, a first behavior that is assigned to the at least one activity set by the user can either be an automatic process performed based on the selected activity (i.e, through a table or logic implement by the original programmer/manufacturer like reminder for "medication"→"whimpering") or manually set by a user through an operating device or the setting means.

In another exemplary embodiment, the at least one activity is not an interaction with the robot and the determining means is configured to determine, after or during the selected behavior is carried out, whether or not the determined activity is the at least one activity and/or whether or not the determined activity is a predetermined activity, which is an interaction with the robot symbolizing/indicating the at least one activity as described above.

In addition, when the determined activity is the at least one activity or the predetermined activity, the selecting means is configured to select, as the second behavior, a behavior representing an acknowledgment signal or a behavior representing no reminder. Therefore, the robot is able to demonstrate both the existence and fulfillment of a certain virtual (e.g. hunger) or real (e.g. charging) need through a dedicated behavior.

On the other hand, when the determined activity is not the at least one activity or the predetermined activity, the selecting means can be configured to select, as the second behavior, a behavior representing an alarm signal or a behavior that differs from the first behavior, in the fact that at least a part of the first behavior is carried out at a higher intensity. In this way, the system adapts the behavior to be more effective.

Alternatively or in addition, the system can recognize the current state/activity of the person and use it to evaluate when a reminder will be effective and/or how to adapt the reminder behavior to be more effective.

In another exemplary embodiment, the intensity of the behavior (e.g. the robot's need) and/or the related behavior can be selected based on the amount of time the person is not performing the respective activity. For this, the system can further comprise a storage means for storing the results of the determining means indicating an amount of time the person is not performing the at least one activity, wherein the robot is configured to carry out at least one part of the first behavior and/or the second behavior at different intensities and to adapt the intensity of the at least one part based on the amount of time the person is not performing the at least one activity, and/or the selecting means selects, from different behaviors that are assigned to the at least one activity, the first behavior and/or the second behavior based on the amount of time the person is not performing the at least one activity, in order to adapt the behavior to the number of fulfilled or not fulfilled reminded activities over a certain period.

The information about the current state, location or activity of the person can be used to determine if a certain reminder condition is met and/or to determine the best or inopportune moment for the reminder, e.g. to not interrupt the person while on the phone and to generate the reminder after or before the call. For this, the determining means is configured to determine the current state of the person based on the information derived from the at least one sensing means and to determine, based on the current state, whether or not the first behavior or the second behavior is to be carried out at an earlier time or a later time with respect to the trigger condition.

Alternatively or in addition, the information about the current state can be used to determine, for example, the attention of the person with respect to the robot and to adapt the reminder in accordance with the attention (current state), wherein the robot is configured to carry out at least one part of the first behavior and/or the second behavior in different intensities and to set the intensity of the at least one part based on the determined state.

In addition, the determining means can be configured to determine an emotional state of the person, a physiological state of the person, an activity performed by the person and/or a predetermined emergency state of the person to determine the optimal time for the reminder and/or to set the intensity.

The robot can be designed as a companion device, i.e. in a way that can be perceived by the person as a "pet", e.g. through a cover that provides pleasant haptics, animal-like shape, facial features such as eyes or mouth, "natural" movement patterns such as head turning, blinking, laying down, animal-like sounds such as purring, panting, humming, squeaking, and behavioral reactions to simple interactions like stroking, petting, calling its name.

In another exemplary embodiment, the robot shows some autonomy and is able to walk/drive on its own to reach different locations within the environment of the person (e.g. an apartment), can interact with certain objects, and in general show some form of continuous behavior.

In order to carry out the first behavior and/or the second behavior, the robot can be configured to move to a predetermined position in the environment of the robot (e.g. the apartment), to move on a predetermined trajectory, to move with a predetermined velocity profile, to perform a predetermined pose, to display a predetermined image and/or text, to output a predetermined sound, to perform a predetermined interaction with an object in the environment of the robot and/or to output a light in a predetermined colour and/or in a predetermined intensity.

In order to carry out the different behaviors, the robot can be configured to move to different positions in the environment of the robot, to move on different trajectories, to move with different velocity profiles, to perform different poses, to display different images and/or texts, to output different sounds, to perform different interactions with the object and/or to output light in different colours and/or different intensities.

To ensure that the person is able to perceive the behavior, the robot can be configured to move to the person or to wait for the arrival of the person at the robot to carry out the first behavior and/or the second behavior.

In order to account for the fact that medication and other items and services can be given to the person by another person, the determining means can be configured to determine, based on the information derived from the at least one sensing means, whether or not the at least one activity is performed by another person in accordance with the condition, wherein the robot is configured to carry out the selected behavior if the at least one activity is performed neither by the person nor by the other person in accordance with the condition.

An interface, either as part of the robot or as an app or program on a computer/smart phone, provides a means for a user (e.g. the person) to define, as the trigger condition, a number of reminder rules which combine schedule information (such as frequency, time, events) with a desired activity out of a number of options (e.g. medication, eating, sleeping) and optionally a grace period or importance/urgency parameter.

In another exemplary embodiment, the trigger condition can define that the at least one activity is to be performed at a certain time or times, with a certain frequency, after, before or during a certain activity or a certain sequence of activities is performed by the person, after or before a certain behavior is carried out by the robot and/or within a certain period of time, and/or the trigger condition defines a grace period for performing the at least one activity and/or a priority of the at least one activity with respect to importance or urgency.

For sensing the person, static sensors, mobile sensors, (e.g. sensors in smart watches or smartphones) or signals indicating actuated devices (e.g. appliances of a smart home system) can be used. In another exemplary embodiment, at least one of the sensing means is configured to detect an operating state of a device controllable by the person.

The following sensor types can be used:
cameras, like 3D cameras, active ("pan-tilt-zoom") cameras, IR cameras;
microphones
physiological sensors, like skin conductance sensors, EMG, EEG, electrodes, optical heart beat sensors, temperature sensors;
magnetic switch sensors, proximity sensors (e.g. Ultra sonic), motion sensors (e.g. optical), pressure sensors (e.g. piezo-electric); and/or
virtual sensors, like for on-screen selection.
Example behaviors of the robot could be:
sitting in a specific position, either defined by an object, e.g. the person, medicine cabinet, water bottle, or a room-related location, e.g., washbasin, entrance door;
facial expressions, e.g. smiling, yawning, closing eyes;
gestures, e.g. waving; or body poses, e.g. lie down, stretch;
general activities like walking around, jumping up & down, turning, dancing;
specific activities like eating from a bowl, scratching a wall, playing with a ball;
changing color, turning its display on/off; and/or
acoustic expressions like laughing, heavy breathing, snoring, purring.

The functions of the setting means, the selecting means and/or the determining means described herein may be implemented using individual hardware circuitry, using software functioning in conjunction with a programmed microprocessor or a general purpose computer, using an application specific integrated circuit (ASIC) and/or using one or more digital signal processors (DSPs). Further, the setting means, the selecting means and/or the determining means can be a part of a processing unit (e.g. computer) or the robot.

The method according to the disclosure for reminding a person to perform at least one activity uses a robot configured to carry out different behaviors and comprises the steps of:
setting, by a user, the at least one activity and its corresponding trigger condition for a reminder;
selecting, from the different behaviors, a first behavior that is assigned to the at least one activity set by the user;
sensing at least the person by at least one sensing means;
determining, based on information derived from the at least one sensing means, whether or not the at least one activity is performed by the person in accordance with the trigger condition;
carrying out, by the robot, the selected behavior if the at least one activity is not performed by the person in accordance with the trigger condition;
determining, after or during the selected behavior is carried out, an activity performed by the person based on the information derived from the at least one sensing means;
selecting, from the different behaviors, a second behavior that is assigned to the determined activity; and
carrying out, by the robot, the second behavior.

The same features are denoted in the figures by the same reference signs.

Figure 1:
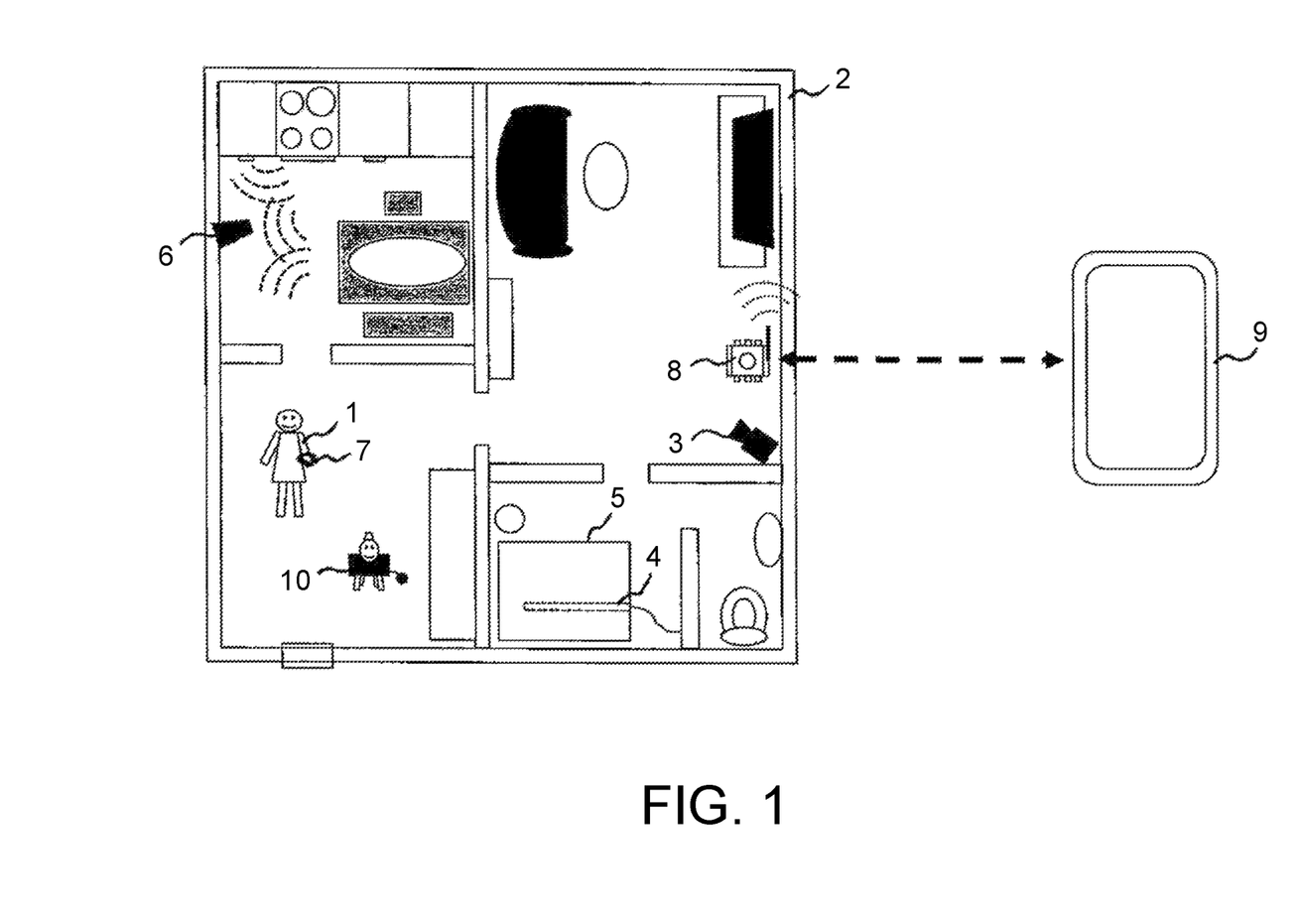
FIG. 1 shows a system according to an exemplary embodiment of the present disclosure.

FIG. 1 shows a system according to an exemplary embodiment of the present disclosure, which reminds a person 1 in an apartment 2 to perform certain activities. The system shown in FIG. 1 comprises a camera 3 that captures an area in the living room, a pressure sensor 4 installed in a bed 5 in the bedroom, a microphone 6 installed in the kitchen, a smart watch 7 worn on the wrist of the person 1, a processing unit 8 like a computer, an operating device 9 (e.g. PC, smartphone, tablet) and a robot 10 that is connected to the processing unit 8 by a radio connection and that reminds the person 1 for self-care related activities by mirroring the related needs through its own behavior at given predefined times or after not detecting a certain activity for a certain time.

The microphone 5 is configured to detect noise emerging from activities of the person 1, like cooking, eating, walking, loud laughter and speaking and to transmit the detected noise to the processing unit 8 via radio frequency communications or cables. The camera 3 generates an image signal from the person 1 in the living room and transmits the image signal to the processing unit 8 via radio frequency communication or cable. The pressure sensor 4 generates a pressure signal that indicates if the person 1 is in the bed 5 or not and transmits the pressure signal to the processing unit 8 via radio frequency communication or cable. The smart watch 7 comprises a plurality of sensors, like an ambient light sensor, a three-axis accelerometer, heart rate monitor and a positioning system (indoor and/or GPS) and is configured to transmit data generated by the sensors to the processing unit 8 via radio frequency communication.

The operating device 9 is connectable to the processing unit 8 and/or the robot 10 to set the certain activities and the corresponding trigger conditions by a user (e.g. the person 1, family member or attending physician), wherein the processing unit 8 or the robot 10 generates a graphical user interface that is displayed on the operating device 9. The activities and trigger conditions set by the user are stored in the processing unit 8 that selects, for each activity set by the user, a behavior of the robot 10 that reminds the person 1 to perform the respective activity. The behavior can be selected based on a table, which assigns a behavior to each activity selectable by the user. Alternatively or in addition a group of behaviors can be assigned to an activity, wherein the processing unit 8 selects a behavior from the group based on the current state of the person 1 (e.g. inattentive, position and environment of the person 1) and/or the trigger conditions (e.g. importance, time).

In the graphical user interface, the use can select one or more of the activities included in the table, the corresponding trigger conditions (reminder schedule setting) and, for at least a part of the activities, whether a reminder is always generated or only if the activity is not performed by the person 1 in accordance with the trigger condition.

The robot is designed as a companion device (e.g. a dog) and is able to walk on its own to reach different locations within the apartment 2. In addition, the robotic device can be designed to show remind-free interaction with the person 1 such as dedicated behaviors in response to touch or speech.

Figure 2:
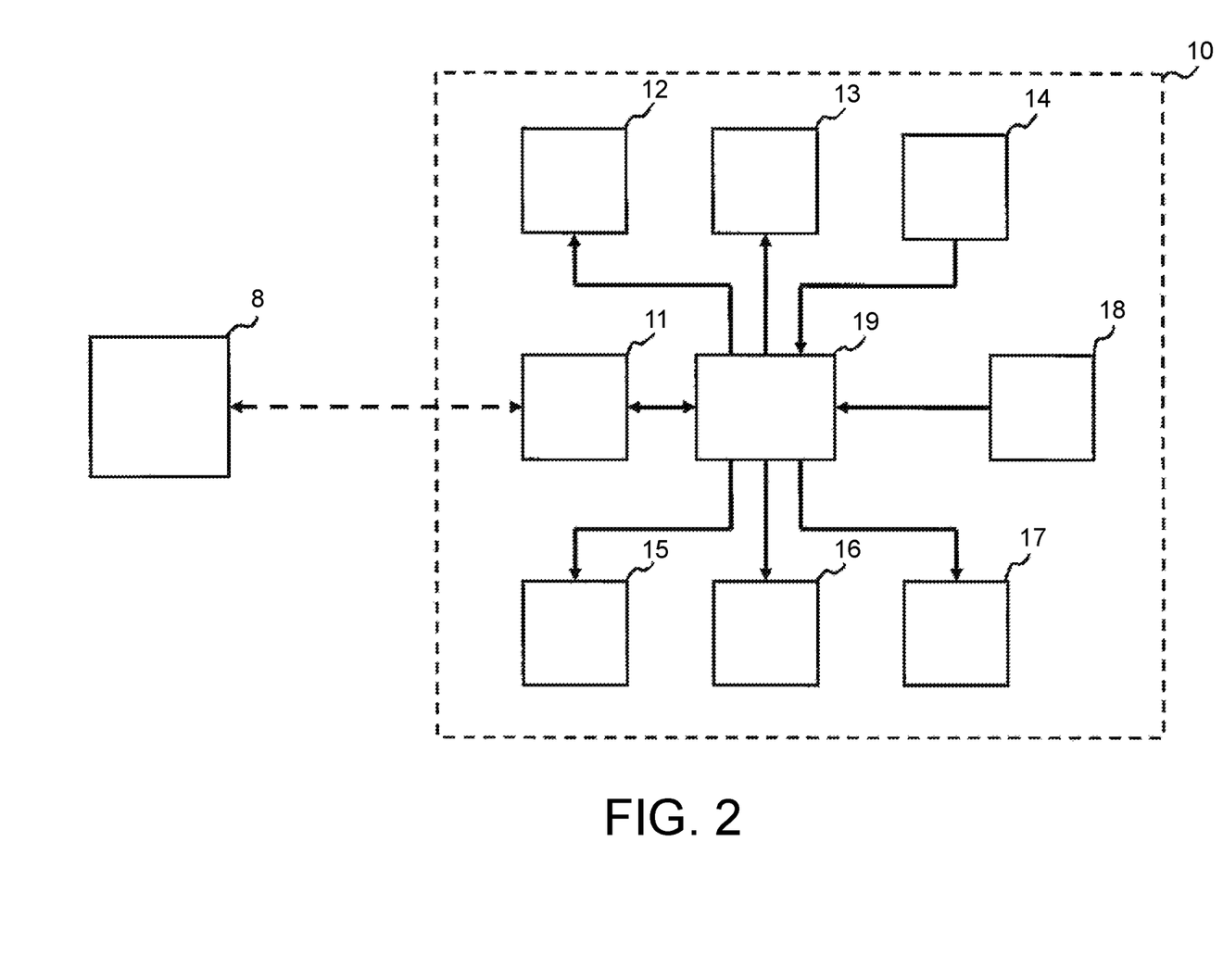
FIG. 2 shows a block diagram of the robot shown in FIG. 1.

FIG. 2 shows a block diagram of the robot 10 that is connected to the processing unit 8. The robot 10 comprises a transmitting and receiving means 11 (e.g. WLAN adapter) that receives information indicating the behavior to be to carried out from the processing unit 8, a display 12 configured to display a symbolic representation of a face, a speaker 13 for outputting sounds, a camera 14 for sensing the environment of the robot 10 (including the person 1), electrically driven legs 15, electrically driven arms 16, an electrically driven tail 17, a touch sensor 18 for detecting an interaction (touch) of the person 1 with the robot 10 and a controlling means 19 that controls the display 12, the speaker 13, the electrically driven legs 15, the electrically driven arms 16 and the electrically driven tail 17 to carry out the selected behavior. The information derived from the camera 14 and the touch sensor 18 are transmitted to the processing unit 8.

The processing unit 8 determines continuously certain states of the person 1 that are relevant to the selected activities and conditions based on the sensor data that are automatically generated by the cameras 3, 14, the pressure sensor 4, the microphone 6, touch sensor 18 and the smart watch 10. If, for example, the activities "taking a first medication twice times a day before a meal", "taking a second medication before going to bed" and "sleeping at least eight hours" are selected by the user, at least the states "cooking", "eating", "taking medication" and "sleeping" are determined, wherein the processing unit 8 detects, in the sensor data, certain characteristics that are assigned to the states.

In particular, the physiological states "sleeping" and "awake" can be detected based on the pressure signal of the pressure sensor 6 and the heart rates measured by the smart watch 9 and the states "cooking", "eating" and "taking medication" can be estimated by image and audio processing based on the image captured by the cameras 3, 14 and the noise captured by the microphone 6.

For each state (state class), one or more characteristics could be determined by a machine learning method trained with labeled noise and/or images (videos) of a person demonstrating the respective state (state class). The processing unit 8 can perform the machine learning method, wherein the states and its corresponding characteristics or the learning data are inputted by the operating device 9.

A behavior of the robot 10 is selected to remind the person 1 to the activity set by the user, wherein the behavior indicates, to the person 1, a need of the robot 10 and an interaction of the person 1 with the robot 10 necessary to fulfill this need is related to the activity set by the user. In this way, the interaction of, for example, presenting the medication to the camera 14 of the robot 10 reminds the person 1 to take the medication for herself. To ensure this, the processing unit 8 evaluates the interaction based on the sensor signals and the behavior is carried out by the robot a second time with higher intensity if the interaction is not correct and/or the person 1 does not take the medication for herself. Alternatively, the robot 10 can give an alarm via the speaker 13 or display the medication on the display 12. A behavior, in which the robot 10 smiles and/or wiggles its tail, is carried out if the interaction is correct and/or the person 1 takes medication for herself. The processing unit 8 can determine the number of fulfilled or not fulfilled correct interactions and/or the number of fulfilled or not fulfilled reminded activities over a certain period. This information can be used to adapt the behavior and/or to select, from the group of behaviors assigned to the activity, a behavior, with which the success rate is increased.

In order to ensure that the person 1 will be able to perceive the behavior that triggers the interaction, the robot 10 walks to the person 1 and/or waiting for the person 1 to be present. For example, when the processing unit 8 determines the state "cooking" and the set activity "taking a first medication twice times a day before a meal" is still outstanding, the processing unit 8 controls the robot 10 to walk to the person 10 in the kitchen and to carry out the behavior assigned to the outstanding activity.

Figure 3:
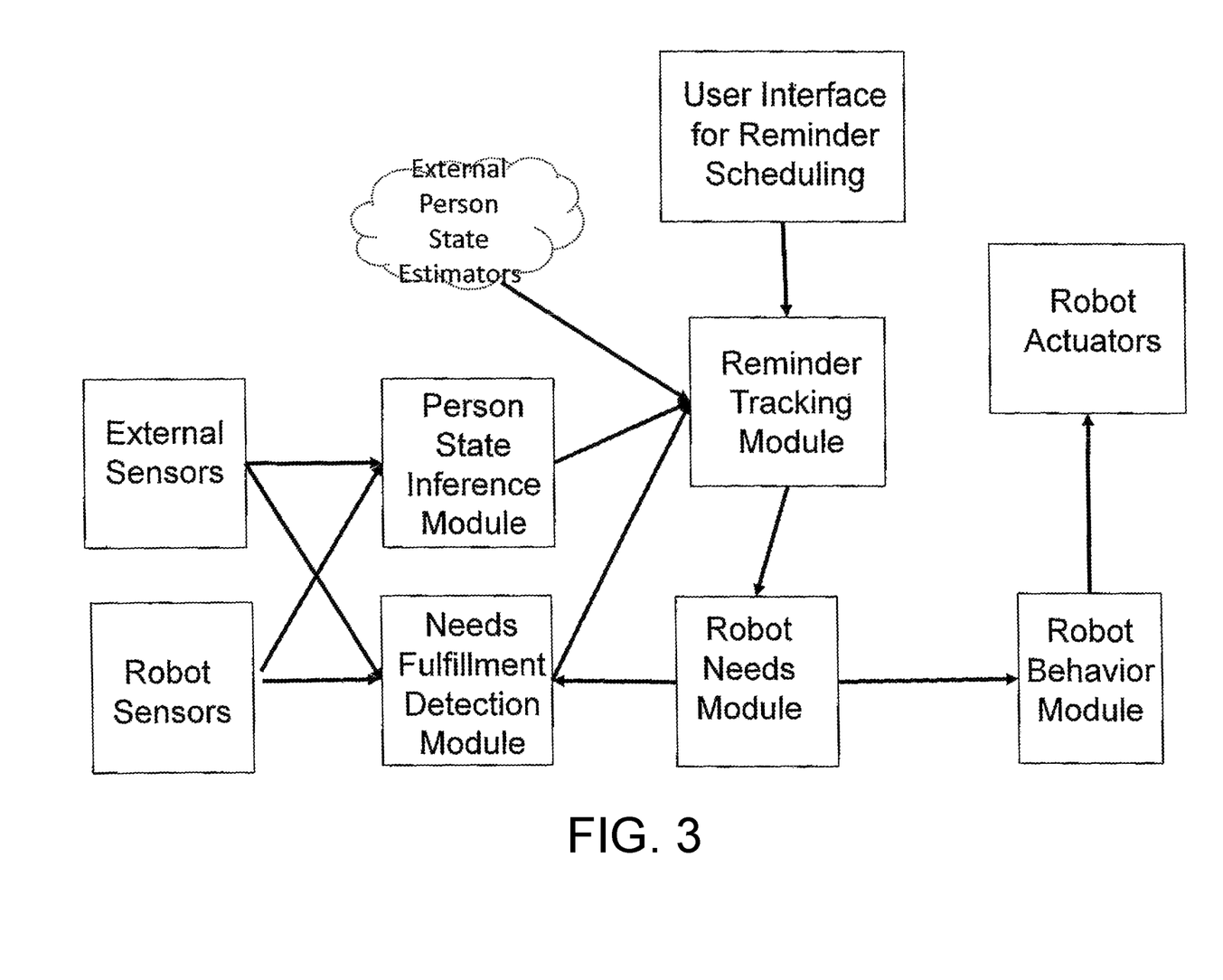
FIG. 3 shows a block diagram of the system shown in FIG. 1.

In a specific implementation, external estimators (e.g. hospital) can provide additional information on the state of the person. FIG. 3 shows the modules of the system according to an exemplary embodiment of the present disclosure.

The system can be configured to remind each of a plurality of persons to perform their respective activity, wherein facial recognition and/or carrying an ID makes it possible to identify individual persons.

Alternatively or in addition, for determining the state of the person, sensors or signals from certain devices, e.g. TV communicating its power status, fridge communicating if door is open, together with a set of predefined rules how to map these signals to assumed states, i.e. "watching TV" or "eating", can be used. Alternatively, all sensors for sensing the person 1 can be installed within the robot 10 or in the apartment 2 (external sensors).

Further, if the reminder setting included a grace period, the processing unit 8 might try to find/predict the best possible reminder timing within this grace period around the determined schedule event. If the reminder setting includes an importance/urgency setting, the processing unit 8 can use this information to determine if interrupting a certain ongoing human activity is acceptable and to specify a strength or temporal strength increase parameter of a robot need and therefore the corresponding behavior. The information about the state can be also used to determine if/when he performed the activity specified in the reminder and eventually adapt the need of the robot accordingly. Accordingly, the processing unit 8 can also use the information to keep track if the person performed the specific activity already before the reminder triggers, and adapt/remove the trigger accordingly.

Figure 4:
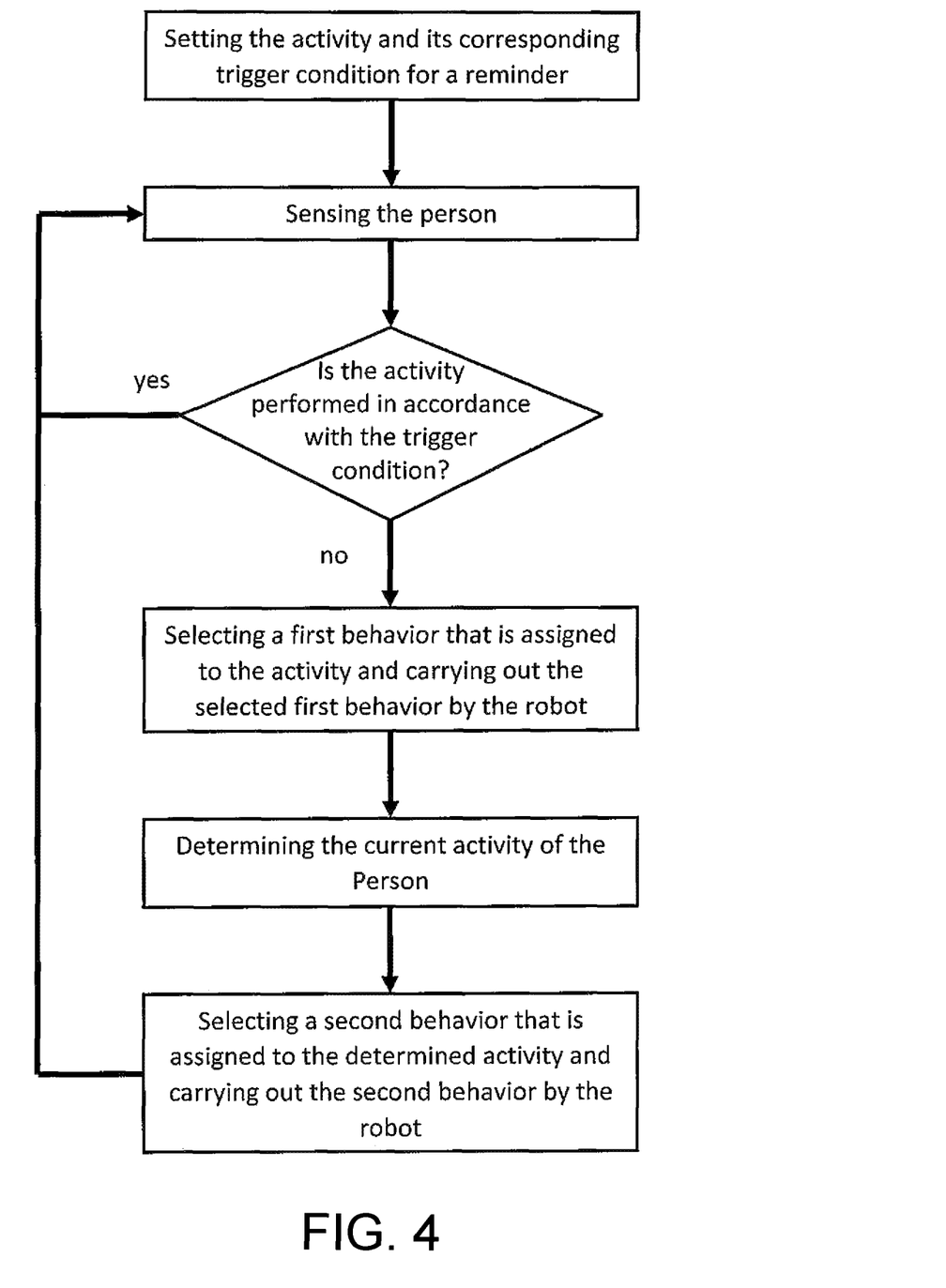
FIG. 4 shows a simplified flow chart for explanation of the method for reminding a person to perform at least one activity using a robot according to the disclosure.

FIG. 4 shows a simplified flowchart showing the single steps performed by the realization of the method described in detail above.

It will be apparent to those skilled in the art that various modifications and variations can be made to the structure of the disclosure without departing from the scope or spirit of the disclosure. In view of the foregoing, it is intended that the present disclosure cover modifications and variations of this disclosure provided they fall within the scope of the following claims and their equivalents.

What is claimed is:

1. A system for reminding a person to perform at least one activity, comprising:
   a robot configured to carry out different behaviors;
   at least one sensor configured to sense at least the person; and
   at least one processor configured to:
      set, by a user, the at least one activity and its corresponding trigger condition for a reminder to perform the at least one activity, wherein the at least one activity is not an interaction with the robot;
      select, from the different behaviors, a first behavior that is assigned to the at least one activity set by the user, wherein the first behavior symbolizes the at least one activity to be performed by the person or indicates a need of the robot or symptom of the robot; and
      determine, based on information derived from the at least one sensor, whether or not the at least one activity is performed by the person in accordance with the trigger condition, wherein:
   the robot is configured to carry out the selected first behavior if the at least one activity is not performed by the person in accordance with the trigger condition and is configured not to carry out the selected first behavior when the at least one activity is performed by the person in accordance with the trigger condition;
   the at least one processor is configured to detect, after or during the selected first behavior is carried out, an activity performed by the person based on the information derived from the at least one sensor;
   the at least one processor is configured to determine whether the detected activity is the at least one activity and to determine whether the detected activity is a predetermined activity, which is an interaction with the robot necessary to fulfil the need of the robot or to alleviate the symptom of the robot;
   the at least one processor is configured to select, from the different behaviors, a second behavior representing an acknowledgment signal when the detected activity is the at least one activity or is the predetermined activity; and
   the robot is configured to carry out the selected second behavior in response to the detected activity being the at least one activity or being the predetermined activity.

2. The system according to claim 1, wherein
when the detected activity is not the at least one activity or the predetermined activity, the at least one processor is configured to select, as the second behavior, a behavior that differs from the first behavior, in the fact that at least a part of the first behavior is carried out in a higher intensity, or a behavior representing an alarm signal.

3. The system according to claim 1, further comprising a memory configured to store an amount of time the person not performing the at least one activity, wherein the robot is configured to carry out at least one part of the first behavior and/or the second behavior in different intensities and to adapt the intensity of the at least one part based on the amount of time the person is not performing the at least one activity.

4. The system according to claim 1, wherein
the at least one processor is configured to determine the current state of the person based on the information derived from the at least one sensor and to determine, based on the current state, whether or not the first behavior or the second behavior is to be carried out at an earlier time or a later time with respect to the trigger condition.

5. The system according to claim 4, wherein
the at least one processor is configured to determine an emotional state of the person, a physiological state of the person, an activity performed by of the person and/or a predetermined emergency state of the person.

6. The system according to claim 1, wherein
the at least one processor is configured to determine the current state of the person based on the information derived from the at least one sensor, and
the robot is configured to carry out at least one part of the first behavior and/or the second behavior in different intensities and to set the intensity of the at least one part based on the determined state.

7. The system according to claim 1, wherein
in order to carry out the first behavior and/or the second behavior, the robot is configured to move to a predetermined position in the environment of the robot, to move on a predetermined trajectory, to move with a predetermined velocity profile, to perform a predetermined pose, to display a predetermined image and/or text, to output a predetermined sound, to perform a predetermined interaction with an object in the environment of the robot and/or to output a light in a predetermined colour and/or in a predetermined intensity.

8. The system according to claim 7, wherein
in order to carry out the different behaviors, the robot is configured to move to different positions in the environment of the robot, to move on different trajectories, to move with different velocity profiles, to perform different poses, to display different images and/or texts, to output different sounds, to perform different interactions with the object and/or to output light in different colours and/or different intensities.

9. The system according to claim 1, wherein the robot is configured to move to the person or to wait for the arrival of the person at the robot to carry out the first behavior and/or the second behavior.

10. The system according to claim 1, wherein the at least one processor is configured to determine, based on the information derived from the at least one sensor, whether or not the at least one activity is performed by another person in accordance with the trigger condition, and the robot is configured to carry out the selected first behavior if the at least one activity is performed neither by the person nor by the other person in accordance with the trigger condition.

11. The system according to claim 1, wherein the trigger condition defines that the at least one activity is to be performed
at a certain time or times,
with a certain frequency,
after, before or during a certain activity or a certain sequence of activities is performed by the person,
after or before a certain behavior is carried out by the robot; and/or
within a certain period of time; and/or
the trigger condition defines
a grace period for performing the at least one activity, and/or
a priority of the at least one activity with respect to importance or urgency.

12. A method for reminding a person to perform at least one activity using a robot configured to carry out different behaviors, the method comprising the steps of:
setting, by a user, the at least one activity and its corresponding trigger condition for a reminder to perform the activity, wherein the at least one activity is not an interaction with the robot;
selecting, from the different behaviors, a first behavior that is assigned to the at least one activity set by the user, wherein the first behavior symbolizes the at least one activity to be performed by the person or indicates a need of the robot or symptom of the robot;
sensing at least the person by at least one sensor;
determining, based on information derived from the at least one sensor, whether or not the at least one activity is performed by the person in accordance with the trigger condition;
carrying out, by the robot, the selected first behavior only when the at least one activity is not performed by the person in accordance with the trigger condition;
detecting, after or during the selected first behavior is carried out, an activity performed by the person based on the information derived from the at least one sensor;
determining whether the detected activity is the at least one activity and determining whether the detected activity is a predetermined activity, which is an interaction with the robot necessary to fulfil the need of the robot or to alleviate the symptom of the robot;
selecting, from the different behaviors, a second behavior representing an acknowledgement signal when the detected activity is the at least one activity or is the predetermined activity; and
carrying out, by the robot, the second behavior.

13. A system for reminding a person to perform at least one activity, comprising
a robot configured to carry out different behaviors;
at least one sensor configured to sense at least the persons; and
at least one processor configured to:
set, by a user, the at least one activity and its corresponding trigger condition for a reminder to perform the at least one activity, wherein the at least one activity is an action that relates to a predetermined object and is not an interaction with the robot;
select, from the different behaviors, a first behavior that is assigned to the at least one activity set by the user, wherein the first behavior symbolizes the at least one activity to be performed by the person or indicates a need of the robot or symptom of the robot;
determine, based on information derived from the at least one sensor, whether or not the at least one activity is performed by the person in accordance with the trigger condition, wherein:
the robot is configured to carry out the selected first behavior if the at least one activity is not performed by the person in accordance with the trigger condition and is configured not to carry out the selected first behavior when the at least one activity is performed by the person in accordance with the trigger condition;
the at least one processor is configured to detect, after or during the selected first behavior is carried out, an activity performed by the person based on the information derived from the at least one sensor;
the at least one processor is configured to determine whether the detected activity is the at least one activity and to determine whether the detected activity is a predetermined activity, which is an interaction with the robot where the person shows the predetermined object to the robot, where the person charges the robot, where the person puts the robot in a box, or where the person throws a ball for the robot to be retrieved;
the at least one processor is configured to select, from the different behaviors, a second behavior representing an acknowledgment signal when the detected activity is the at least one activity or is the predetermined activity; and
the robot is configured to carry out the selected second behavior in response to the detected activity being the at least one activity or being the predetermined activity.

14. A method for reminding a person to perform at least one activity using a robot configured to carry out different behaviors, the method comprising the steps of:
setting, by a user, the at least one activity and its corresponding trigger condition for a reminder to perform the activity, wherein the at least one activity is an action that relates to a predetermined object and is not an interaction with the robot;
selecting, from the different behaviors, a first behavior that is assigned to the at least one activity set by the user, wherein the first behavior symbolizes the at least one activity to be performed by the person or indicates a need of the robot or symptom of the robot;
sensing at least the person by at least one sensor;
determining, based on information derived from the at least one sensor, whether or not the at least one activity is performed by the person in accordance with the trigger condition;
carrying out, by the robot, the selected first behavior only if the at least one activity is not performed by the person in accordance with the trigger condition;

detecting, after or during the selected first behavior is carried out, an activity performed by the person based on the information derived from the at least one sensor, determining whether the detected activity is the at least one activity and determining whether the detected activity is a predetermined activity, which is an interaction with the robot where the person shows the predetermined object to the robot, where the person charges the robot, where the person puts the robot in a box, or where the person throws a ball for the robot to be retrieved;

selecting, from the different behaviors, a second behavior representing an acknowledgment signal when the detected activity is the at least one activity or is the predetermined activity; and carrying out, by the robot, the second behavior.

\* \* \* \* \*